United States Patent [19]

Lewyn

[11] 4,258,719

[45] Mar. 31, 1981

[54] HEART RATE MEASUREMENT SYSTEM

[75] Inventor: Lanny L. Lewyn, Laguna Beach, Calif.

[73] Assignee: Hughes Aircraft Company, Culver City, Calif.

[21] Appl. No.: 965,816

[22] Filed: Dec. 4, 1978

[51] Int. Cl.³ ............................................. A61B 5/02
[52] U.S. Cl. ............................ 128/690; 307/311; 328/2
[58] Field of Search ................. 128/687–690; 328/165, 2, 167; 307/231, 311; 250/214 A, 214 AL, 214 B, 214 C, 215

[56] References Cited

U.S. PATENT DOCUMENTS

| | | | |
|---|---|---|---|
| 3,328,590 | 6/1967 | Kapsambelis | 250/214 B |
| 3,408,578 | 10/1968 | Smith | 250/214 AG |
| 3,790,288 | 2/1974 | Hostetter | 250/214 |
| 3,857,047 | 12/1974 | Knight | 307/231 |
| 3,970,840 | 7/1976 | De Bruine | 250/214 B |
| 4,047,023 | 9/1977 | Key et al. | 250/214 B |
| 4,063,551 | 12/1977 | Sweeney | 128/690 |
| 4,166,454 | 9/1979 | Meijer | 128/689 |

Primary Examiner—Robert W. Michell
Assistant Examiner—Francis J. Jaworski
Attorney, Agent, or Firm—W. H. MacAllister; Walter J. Adam

[57] ABSTRACT

A pulsed IR reflectance plethysmograph for heart rate measurement and display in a digital watch or as a medical instrument using, for example, a pulsed LED light emitting diode for transmitting light pulses and a photodiode for receiving light pulses reflected from a finger. The LED and photodiode are mounted in a small sensor on the watch or medical instrument. The photodiode is connected directly to a signal conditioning circuit which rapidly removes unwanted asynchronous ambient background light signals such as from sunlight, by means of a switched ambient light subtractor circuit which performs the subtraction without requiring amplification or conversion of the detector signal photocurrent to another electrical parameter. The signal current after cancellation of the ambient background signal is sampled in an integrate and hold circuit to provide a heart systolic pressure wave. The synchronous steady state IR pulse carrier envelope signal is cancelled by a perfect second-order feedback loop via an integrating amplifier and a switched transconductance element that operates with fast response, even under conditions of large overloads that occur at the sensor. Pulses of the heart systolic pressure wave are then detected to determine the pulse rate which is displayed. When only the presence of an unmodulated IR light carrier is to be detected, as in an IR light beam detector, an ambient light subtractor in accordance with the invention is provided in an unswitched configuration that removes ambient light with a minimum number of components over an extremely wide dynamic range.

25 Claims, 11 Drawing Figures

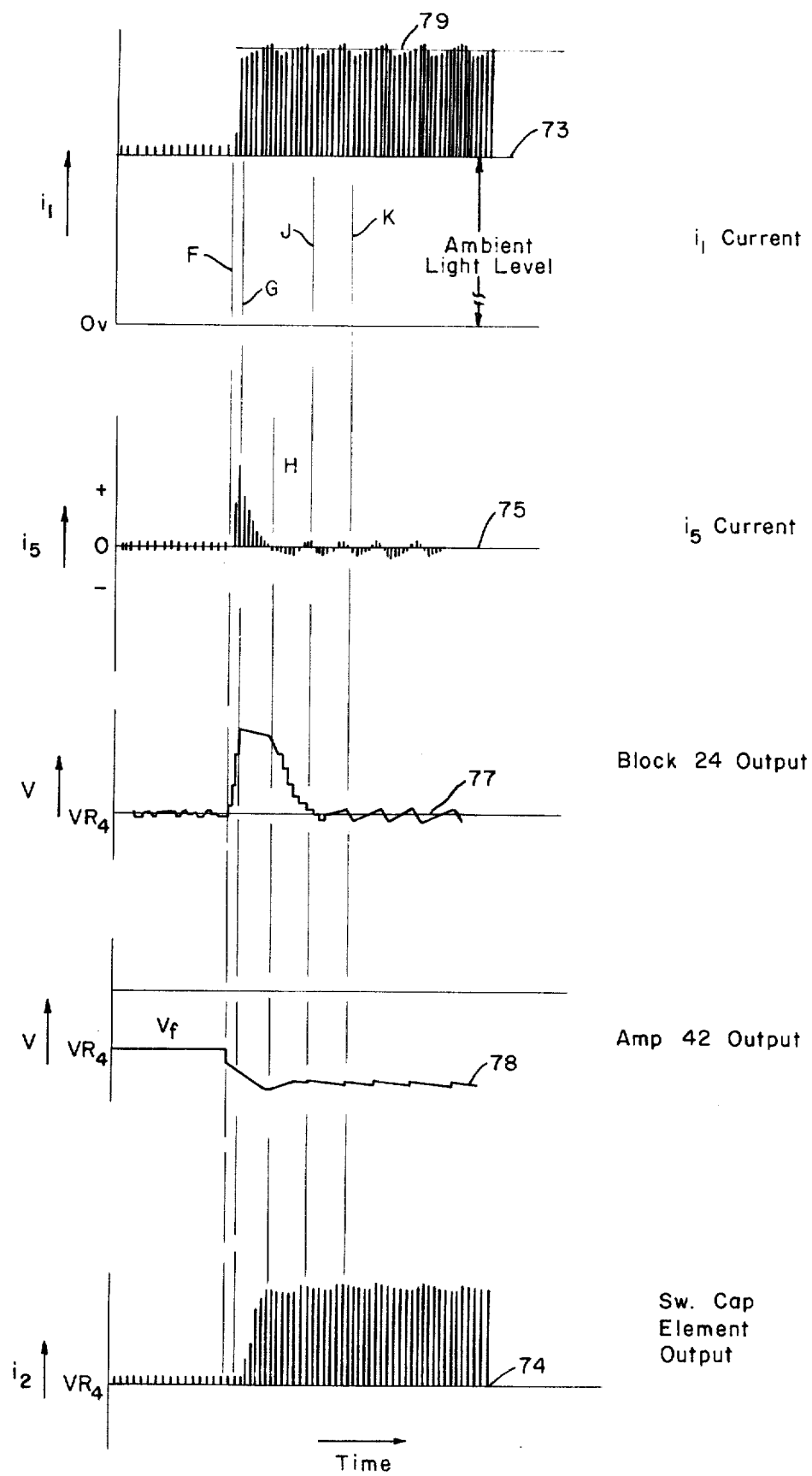

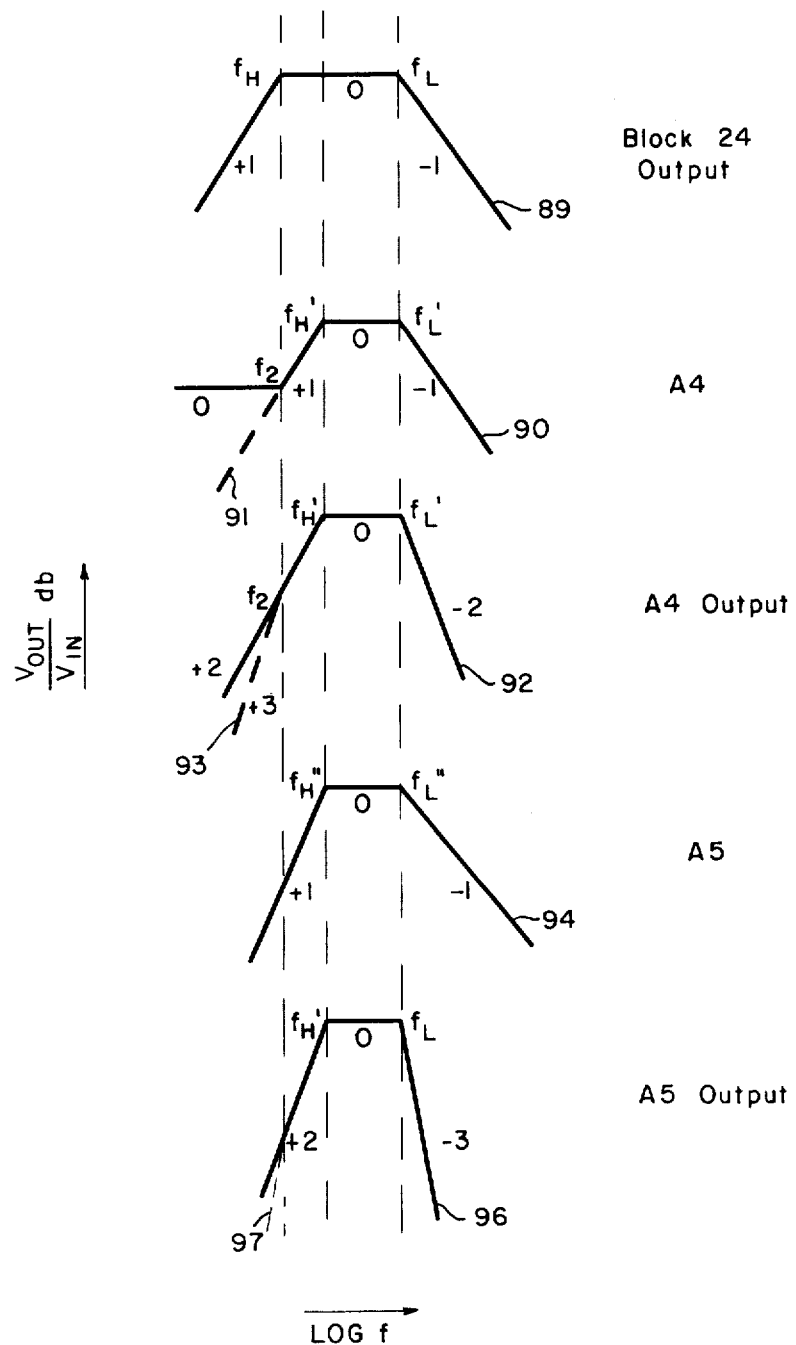

HEART RATE MEASUREMENT SYSTEM

BACKGROUND OF THE INVENTION

This invention is related to pulse rate measurement systems, and particularly to an improved pulse rate measuring system that provides a fast response for cancelling undesired noise signals and that rapidly and accurately develops pulse rate readings with minimum power and voltage level requirements.

In many systems, it is necessary to use a photodetector in ambient light to detect small pulses of light from a source, and to either determine the amplitude of the pulses, the rate of the pulses, or both the amplitude and rate of the pulses. One particular use of a photodetector in an ambient light situation is a pulsed infrared (IR) reflectance plethysmograph for heart rate measurement that may be integrated into a wristwatch or may be a medical instrument suitable for clinical use. The instrument in accordance with the invention is called a plethysmograph because it measures heart rate by measuring the change in size of the capillaries or blood vessels in a finger, for example, which change in size varies the reflectance characteristics of the capillaries to light energy (the capillaries dilate upon the arrival of the systolic pressure wave and the reflectance drops). Another use of a photodetector in high intensity ambient light may be an electronic game. For reliable operation of the plethysmograph, game, or the like, in ambient light, it is necessary to provide some means between the photodetector and the utilization system that has the ability to reject high levels of ambient light, even sunlight, to reject other undesired signals, and to maintain a fast response time.

In a plethysmograph system for measuring pulse rate when a finger is placed in a position so that the photodetector can sense reflected light pulses, the result is a temporary overload in the signal detection and amplification circuits. It is possible to sense this overload condition and use a feedback bias control to change the operating point of the phototransmitter or the photodetector to compensate for the background light level, but for fast response to 120 Hz background flourescent lighting this compensation must be done on a pulse-by-pulse basis. Another problem of a feedback bias control arrangement is overcorrecting to the point of suppressing the desired light pulses as well as the ambient light signal. This suppression of the desired light signal will normally occur with any electric feedback overload correction system which cannot distinguish between the ambient light components and the pulsed light. Under extreme overload conditions, this feedback bias control arrangement may require 20 to 30 seconds to stabilize to the point that accurate readings are provided, especially if the system is powered from a relatively low voltage power supply such as the 3 v battery supply of a digital wristwatch. Another possible solution of the overload problem comprises the generation of a reset command to be applied when the condition of overload is sensed.

An alternate approach to this problem of obtaining a useable signal in a relatively short time is to separate the desired light pulse signal from the unwanted background ambient light signal by amplifying the light pulse signal plus ambient signal, and converting it to a stored charge or voltage so that the amplitude of the unwanted ambient signal can be removed by a high level differencing (subtraction) circuit. This amplification of both the pulse signal plus the background signal prior to differencing, results in severe dynamic range limitations in those usual cases where the ambient light signal and amplitude is several thousand times greater than the pulsed light signal amplitude and where power supply voltages are limited such as in a digital wristwatch. Moreover, the process of determining the level of the ambient light signal to be subtracted may require 20 to 30 seconds to stabilize in a 3 volt system. A prior art pulse rate measuring system that amplifies the input signal is taught in U.S. Pat. No. 3,980,075, "Photoelectric Physiological Measuring Apparatus" by James E. Heule. Another prior art pulse rate measuring system in the form of a watch has been sold by the Pulsar Company and although the circuit arrangement is not known to me, it is believed that the watch does not respond satisfactorily in the presence of high amplitude ambient light such as direct sunlight. A pulse rate system that amplifies the photodetector current for providing a feedback signal to control the LED intensity and that utilizes a sample and hold circuit without prefiltering has been developed by others and requires 20 to 30 seconds to stabilize or else requires a separate control system which provides an initialization command upon sensing that no output signals have been produced for several seconds.

A system which requires 20 to 30 seconds to stabilize would not be acceptable without an initialization command for the plethysmograph where it is desirable to measure the heart rate immediately after exercise. If a delay of about 10 seconds is required before measurement can be made, the subject will have had some rest, enough to possibly allow the heart rate to decrease from the peak level. Also, in order to conserve time and provide timely data, a heart rate instrument for use by medical personnel should necessarily respond in much less time than 20 to 30 seconds. In all of these examples, as in others that may occur to those skilled in the art, it would be desirable to provide a light pulse detector system with ambient light rejection and other undesired signal rejection that automatically stabilizes in 2 to 3 seconds in order for it to be used for the intended purpose.

SUMMARY OF THE INVENTION

In an exemplary embodiment of the invention, a pulsed IR reflectance plethysmograph for heart rate measurement such as, for example, in a digital watch, is provided having a pulsed light source such as a pulsed LED applying the pulses of light to a finger for reflection to a detector such as a photodiode. A novel gated circuit is connected directly to the photodiode for pulse-by-pulse cancellation of the asynchronous ambient light components of the photocurrent signal without requiring the signal to be amplified or converted to another electrical parameter such as charge or voltage. A switched integrate and hold circuit responds to the current signal after ambient light cancellation to provide a signal representative of the blood pressure modulation. A switched transconductance element, an integrating operational amplifier, and the integrate and hold circuit are included in a perfect second-order feedback loop to develop current pulses for cancellation of synchronous IR carrier steady state photocurrent resulting from the pulsed light source. The ambient light cancellation circuit includes a first split-drain FET (field-effect transistor) of one conductivity type (such as P channel) that has its source electrode connected directly to the photodiode. Half of the photocurrent through the first FET is supplied by a first split-drain electrode to a signal current output node and in turn, to the first split-drain electrode of a second split-drain FET of opposite conductivity type (N channel). The other half of the photocurrent is supplied by the other split-drain electrode of the first FET to a second drain of the second split-drain FET as well as through a first gate to a storage capacitor that is coupled between the gate and the source electrodes of the second FET. The storage capacitor is charged during intervals between IR carrier pulses through the first gate to the level required to maintain both drain currents of the second FET at a value of one-half the source input photocurrent of the first FET. The second split-drain electrode of the second FET absorbs from the output of the first split-drain electrode of the first FET a current equal to half of the ambient light during the period between pulses. During an IR pulse, the first gate is closed (nonconductive) to allow the stored charge of the capacitor to maintain the same level of first drain current in the second FET equal to the current that flowed in the drain electrodes thereof, during the time prior to the IR pulse, and a second gate is opened (conductive) to allow the second drain electrode of the first FET to maintain its conduction at one-half the sum of the IR light pulse (if not cancelled) plus the asynchronous ambient light current. The result is cancellation during the IR pulse periods of ambient light photocurrent from the circuit output current. For cancellation of the synchronous steady state component of the pulse envelope from the detector output signal, the integrate and hold circuit receives the output current during pulse intervals and is connected to a perfect second-order feedback loop including a switched capacitor transconductance element that during pulse intervals provides a feedback proportional to the difference between the output voltage of an integrating operational amplifier, $V_f$, and a reference voltage $VR_4$. Until a LED pulse is generated, the reference voltage $VR_4$ is switched through the transconductance element, and during the time of a pulse, the transconductance element is switched to receive $V_f$ to provide, for being subtracted from the photodiode current, a feedback charge proportional to the voltage difference $VR_4-V_f$. The heart pressure voltage signal at the output of the integrate and hold circuit is amplified then applied to a discriminator that detects the systolic pulses for computing and displaying a pulse rate. In arrangements where only the detection of an unmodulated IR carrier is required, the asynchronous ambient light detector is used with a resistor replacing the first gate and the second gate being omitted. In this arrangement in which only ambient light is required to be rejected, a resistor and capacitor are chosen to provide the equivalent of a high-pass filter to reject ambient light with a cutoff frequency just below the frequency of the IR modulation.

It is therefore an object of this invention to provide an improved pulse rate measurement system.

It is a further object of this invention to provide a plethysmograph for heart rate measurement that rapidly cancels undesired signals and provides a reading with a minimum of delay.

It is another object of this invention to provide a pulse rate measuring system that responds rapidly with a low voltage power supply and with low power requirements.

It is still another object of the invention to provide an improved ambient light cancellation circuit.

It is another object of this invention to provide an improved light cancellation circuit for use when only asynchronous ambient light is to be cancelled.

BRIEF DESCRIPTION OF THE DRAWINGS

These and other objects, features and advantages of the invention itself, will become apparent to those skilled in the art in the light of the following detailed description taken in consideration with the accompanying drawings, wherein like reference numerals indicate like corresponding parts throughout the several parts wherein:

FIG. 6 is a schematic diagram of waveforms of voltage and current as a function of time for further explaining the operation of the system of FIG. 1;

FIG. 10 is a schematic drawing of diagrams showing the output to input voltage ratio in decifels as a function of log f for explaining the amplifier and bandpass filter of FIG. 9.

DESCRIPTION OF THE PREFERRED EMBODIMENTS

Figure 1:
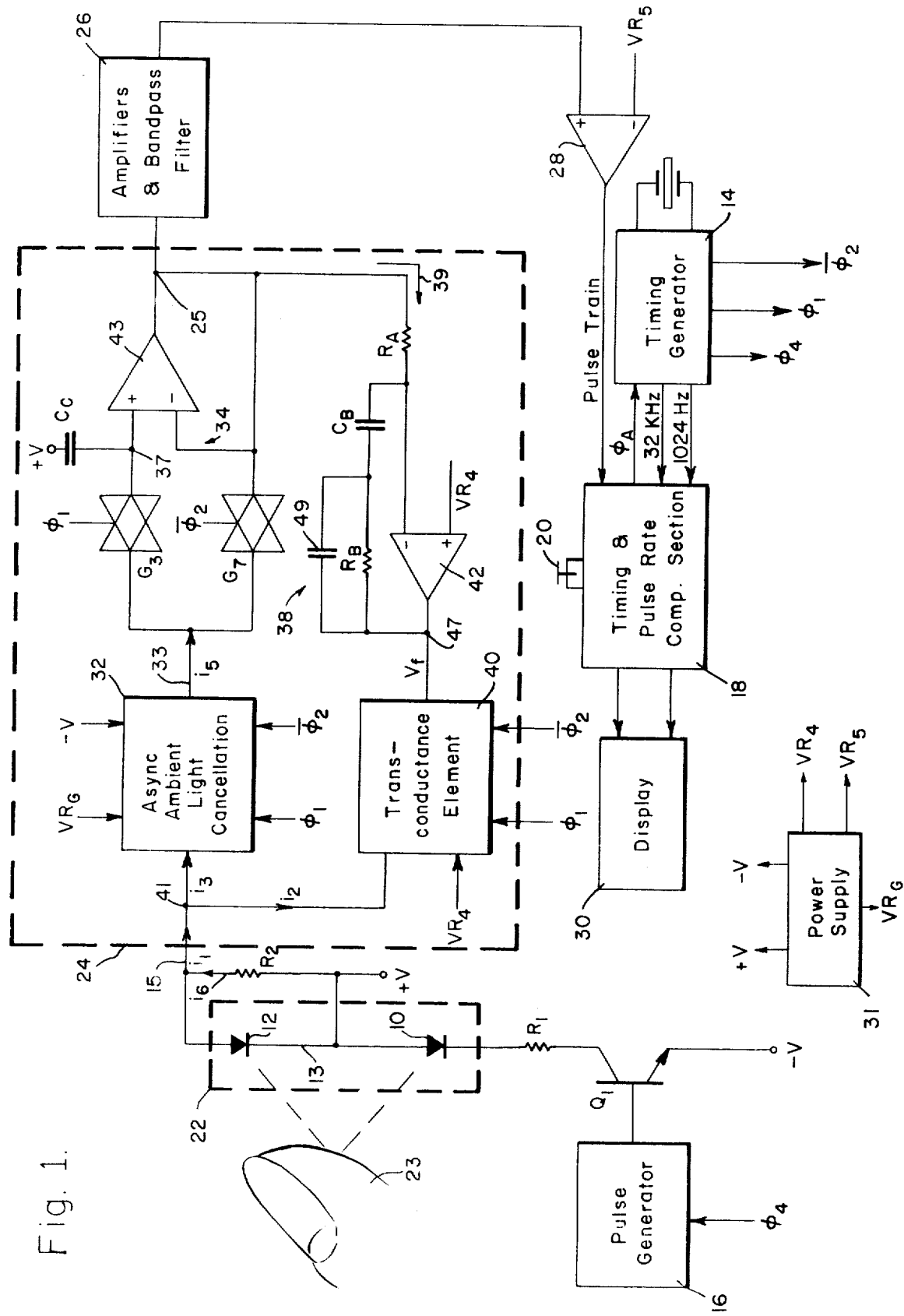
FIG. 1 is a schematic block diagram of a pulsed IR reflectance plethysmograph system for heart rate measurements illustrated in a wristwatch as an example of one use of the concepts in accordance with the invention.

Referring first to FIG. 1, one embodiment of the invention is a plethysmograph adapted to fit in the case of a digital wristwatch for use in field measurements of heart rate, such as by a jogger immediately upon stopping, or while resting, for use by a person who must measure his heart rate frequently, or for use by medical or related personnel. It is to be understood that the principles of the invention are not limited to wristwatches but also apply to instruments that may have other forms such as those that may be desirable for field or hospital uses. More particularly, the illustrated embodiment is a heart rate measurement device which uses the IR reflectometer principle for peripheral pulse measurement by sensing volumetric variations of the capillaries of the fingers or of any tissue with sufficient capillary development to provide a useful light absorption signal. It is to be noted that the invention includes operation at any suitable IR or other wavelengths at which there is suitable penetration through tissue to respond to the blood pressure variations and is not to be limited to any particular wavelength band. The illustrated system utilizes an infrared (IR) light emitting diode (LED) 10 to provide a pulsed source of IR light which is reflected off of the tissues of the finger, for example, and onto a photodiode detector diode 12 having a photocurrent response characteristic. The peripheral systolic wave causes an abrupt increase in IR light absorption (the reflectance drops) by the capillaries of the finger which dilate in response to the systolic pressure wave. The small ($\sim 2\%$) changes or modulation in reflected light amplitude is sensed by the photodiode 12 along with the steady state component of the reflected IR light pulse train plus ambient light from any other source such as sunlight or indoor lighting.

In some prior art IR reflectometer systems, where the light source is not chopped or pulsed, the pulse pressure wave signal is separated from the background ambient light by means of a bandpass filter. While rejection of indoor lighting noise is quite simple in such a system, small changes in large amplitude ambient light signals such as sunlight, are difficult to separate from the pulse pressure wave signal by linear filters.

In the prior art pulsed IR reflectometer systems, a significant amount of LED power is saved since the pulse duty cycle is small and the LED current is adjusted by means of a feedback loop to provide just enough signal to drive the photodetector to a predetermined output level. This saving of power is especially important in a wristwatch operated by very small batteries. Unfortunately, in a pulsed system, the LED feedback system significantly increases difficulties in rejecting unwanted background light noise above (120 Hz indoor lighting) and below (sunlight) the linear filter passband. Problems in rejecting high frequency noise arise if the system employs a sample and hold circuit without prefiltering. Indoor lighting noise is aliased or converted to a lower or beat frequency of a harmonic of the sampling or LED pulse frequency and the 120 Hz light frequency. If the sampling frequency is not chosen well, the beat frequency may lie close to the upper corner frequency of the system amplifier and filter passband. This condition increases sensitivity to indoor light (120 Hz) noise, reduces the maximum intensity of light which can be rejected or places restrictions on the system filter upper corner frequency and response time.

Also, as noted above, an LED drive feedback system results in increased difficulty in rejecting noise signals below the system passband, namely sunlight noise. If the feedback loop cannot distinguish between unacceptable high levels of LED drive and a high level of sunlight, then under direct daylight conditions the feedback loop responds to shut off the LED drive. Consequently, in the system in accordance with the invention as illustrated in FIG. 1, the LED 10 is driven in an open loop with constant current pulses so that the LED drive and front end gains are therefore set at optimum levels and these levels do not and need not change as a result of background lighting conditions or tissue reflectivity. The LED 10 is also driven at a fixed rate set by timing or clock pulses $\phi_4$. A crystal oscillator and pulse system timing generator 14 provides the timing pulses $\phi_4$ which are typically at 73 Hz (to insure that the indoor lighting frequency is well above the system passband) to a base current pulse generator 16, which in turn applies pulses to the base of an NPN type drive transistor $Q_1$. The emitter of the transistor $Q_1$ is coupled to a negative supply voltage, $-V$, and the collector is coupled through a resistor $R_1$ to the cathode of the LED 10. The anode of the LED 10 is coupled through a lead 13 to the positive supply voltage, $+V$, and to the cathode of the photodiode 12 which in turn has its anode coupled to a lead 15. A resistor $R_2$ is connected to the $+V$ supply (lead 13) and to the lead 15. The transistor $Q_1$ conducts pulses of current through the LED 10 and through the current limiting resistor $R_1$ when an analog power control signal $\phi_A$ is turned on. A digital watch timing and pulse rate computation section 18 of a digital watch provides the control signal $\phi_A$ to the timing generator 14 once the operator depresses a push button switch 20. When the switch 20 is depressed a second time, the control signal $\phi_A$ is then turned off. The LED 10 in the illustrated watch system, is mounted in a small sensor 22 illustrated as a dotted box on the face of the watch to pass or transmit IR pulses to the surface of a finger 23, for example, of the person whose pulse rate is being monitored. The IR pulses reflected off the tissue and capillaries of the finger 23 are received by the photodetector 12, also mounted in the sensor 22. The timing generator 14 which responds to a crystal oscillator as is well known in the art, provides the timing signal $\phi_4$ as well as timing signals $\phi_1$ and $\overline{\phi}_2$ for use in the system. Also, the timing generator 14 applies suitable signals such as a 32 KHz clock signal and 1024 Hz signal to the computation section 18.

An input signal current conditioning section 24 directly coupled to the photodiode anode through the lead 15, cancels asynchronous ambient light (sunlight, or artificial light as well as other light asynchronous to the system) and synchronous steady state components of the LED light pulse carrier. The output of the signal conditioning section 24 passes through a node 25 to an amplifier and bandpass filter 26, a heart pressure wave voltage having systolic pulses occurring at a rate that is typically 60 to 80 per minute but which can also be as high as 199 pulses per minute. A voltage level discriminator 28 which provides a comparison of the heart pressure wave voltage relative to the threshold voltage $VR_5$, detects these systolic pulses from a signal provided by the amplifier and bandpass filter 26, and transmits a pulse train of rate determining pulses to the digital watch timing and pulse rate computation section 18 which detects the time (T) between the edges such as the positive going leading edges of the systolic pulses in the train, and computes the pulse rate R ($R = I/T$, where I = the total timing interval. The type of computations provided by the section 18 are well known in the digital art and need not be explained in further detail. The pulse rate R is then displayed as a decimal number by a digital watch display section 30.

A suitable power supply such as a battery power supply 31 is provided and may include a pair of batteries (not shown) that together provide a voltage of approximately 3.2 volts between the voltages $+V$ and $-V$ as utilized in the illustrated heart rate monitoring system in a watch. The power supply 31 also provides voltages $VR_4$, $VR_5$ and $VR_G$. The voltage $VR_5$ for the discriminator 28 is provided for example, by a series string of five diodes, coupled between $+V$ and a constant current generator source with the voltage $VR_5$ being provided at the cathode of the diode that is coupled to the constant current source. The voltage $VR_4$ is the voltage at the anode of the last diode that is coupled to the constant current source. It is to be noted that the discriminator 28 triggers on any signal from the amplifier and bandpass filter 26 that exceeds the difference between the discriminator reference voltage $VR_5$ and the amplifier quiescent output voltage $VR_4$. The voltage $VR_4$-$VR_5$ is typically one diode drop or approximately 0.5 volts.

The input current conditioning section 24 includes an asynchronous ambient light cancellation circuit 32 coupled to the lead 15 to receive a photocurrent $i_3$ which is a current $i_1$ as provided by the photodiode 12 (and a small current $i_6$ from the diode bias resistor $R_2$) combined at a node 41 with the synchronous carrier supression current $i_2$. The ambient light current cancellation circuit 32 also receives the reference voltage $VR_G$ and the timing pulses $\phi_1$ and $\bar{\phi}_2$ for providing carrier cancellation during the smapling pulse periods, and applies an output current $i_5$ on a lead 33 to an integrate and hold circuit 34. Gates $G_3$ and $G_7$, an integrate and hold capacitor $C_c$ and a unity gain amplifier 43 are all included in the integrate and hold circuit 34. The gate $G_3$ responsive to timing signal $\phi_1$ for being biased into conduction is coupled between the lead 33 and a node 37 which in turn is coupled to a positive input terminal of the unity gain amplifier 43. The capacitor $C_c$ is coupled between a $+V$ terminal and the node 37 to provide integration of the signal for applying a blood pressure wave to the node 25. A gate $G_7$ is coupled between the lead 33 and the negative feedback input terminal of the unity gain amplifier 43, as well as to the node 25. The gate $G_7$ is biased into conduction in response to the timing signal $\bar{\phi}_2$ to prevent the parasitic capacitance in the circuit at the lead 33 from being charged during the interval between LED pulses.

A second order feedback loop 39 includes in an operational integrator 38, a resistor $R_A$, an integrating capacitor $C_B$, a stabilizing resistor $R_B$, an integrating operational amplifier 42, and includes a switched capacitor transconductance element 40, for providing the current $i_2$ to or from the node 41 at the lead 15. The resistor $R_A$ is coupled between node 25 and a negative feedback terminal of the amplifier 42, with the negative terminal feedback being derived serially through the integrating capacitor $C_B$ and a stabilizing resistor $R_B$ in turn coupled to a lead 47 at the output of the amplifier 42. A high frequency bypass capacitor 49 is connected across the resistor $R_B$. A reference voltage $VR_4$ is applied to the positive input terminal of the operational amplifier 42. The switched capacitor transconductance element 40 receives the amplifier 42 output signal $V_f$ on the lead 47, the reference voltage $VR_4$ and the timing pulses $\phi_1$ and $\bar{\phi}_2$, to provide the $i_2$ correcting current to the node 41 which cancels the steady state component of the synchronous pulse carrier as well as corrects any residual imbalance remaining after ambient light cancellation by the circuit 32.

To further explain the overall operation of the system in accordance with the invention, the illustrated base current pulse generator 16 provides a 31 μs pulse of 2 mA to the base of the drive transistor $Q_1$ every 13.67 ms i.e., at a 73 Hz rate. The photodiode current is routed to the input signal conditioning section 24 where ambient background light and the synchronous steady state component of the LED light pulse carrier are removed by cancellation. The heart pressure wave voltage signal which is the envelope of the detected photocurrent pulses, is processed by the amplifier and bandpass filter 26 to remove any remaining finger motion artifact signal as well as any background light signals which have not been completely cancelled by the input signal conditioning circuit 24. The voltage level discriminator 28 triggers on any amplifier output greater than the difference between two reference voltages $VR_5$ and $VR_4$ to apply a pulse train to the computation section 18.

Figure 2:
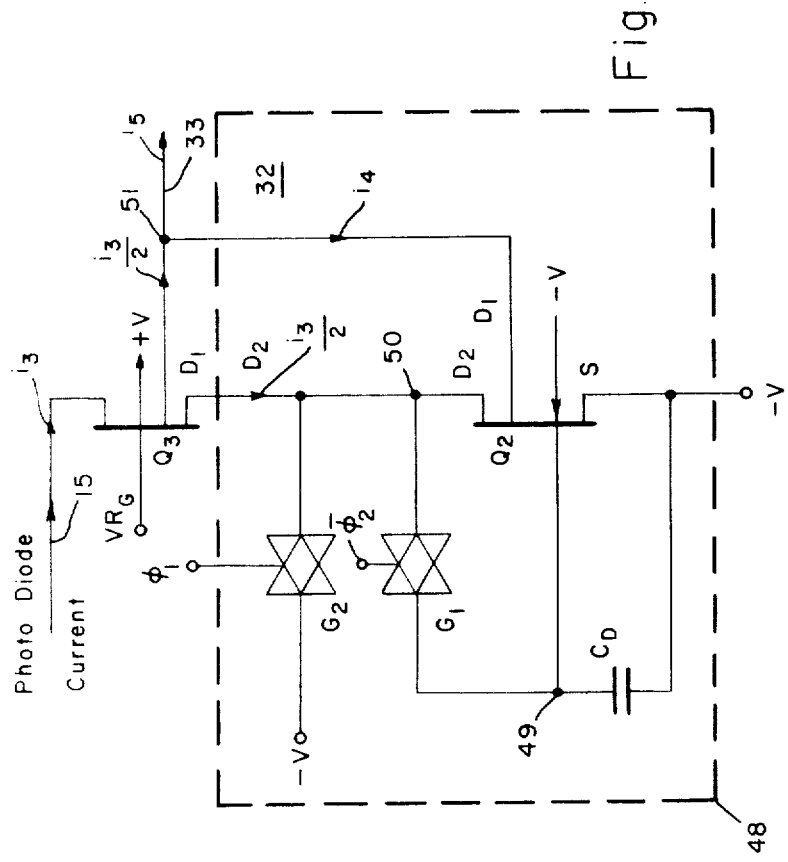
FIG. 2 is a schematic circuit diagram of the improved asynchronous ambient light cancellation circuit shown in the system of FIG. 1.

The input signal conditioning section 24 will now be explained in further detail starting with the asynchronous ambient light cancellation function which is carried out by a split-drain P channel MOS field-effect transistor $Q_3$ and the circuit of a dotted line block 48 as shown in FIG. 2. Operation of the ambient light cancellation circuit 32 may best be understood by first describing that portion of the circuit enclosed in the block 48 which functions as a "storage current mirror" to maintain drain current $i_4$ to a drain electrode $D_1$ of a split-drain N-channel MOS field-effect transistor (FET) $Q_2$ approximately equal to the drain current $i_3/2$ in a drain electrode $D_2$ of the split-drain P-channel FET $Q_3$, so long as a transmission gate $G_1$ is open (conducting) and a transmission gate $G_2$ is closed (not conducting). The split-drain FET $Q_3$ has its gate electrode coupled to a voltage reference terminal $VR_G$ and its substrate biased to $+V$ volts. The photodiode current is applied directly to the source electrode of the FET $Q_3$ without amplification or conversion to another electrical parameter and drain electrode $D_1$ thereof is directly connected to the output current lead 33. The gate $G_1$ responsive to the timing signal $\bar{\phi}_2$ is coupled between a gate node 49 and a node 50, the latter node being coupled between the drain electrode $D_2$ of the FET $Q_3$ and a drain electrode $D_2$ of the FET $Q_2$. Also, a gate $G_2$ responsive to the timing pulse $\phi_1$ is coupled between the negative supply voltage $-V$ and the node 50. The drain electrode $D_1$ of the FET $Q_2$ is coupled to a node 51 and the output lead 33 and the source electrode of the FET $Q_2$ is coupled to the negative supply $-V$ voltage terminal. The well of the FET $Q_2$ is biased by the voltage $-V$. A capacitor $C_D$ is coupled between the gate node 49 and the $-V$ voltage supply. When the transmission gate $G_1$ is conducting, the current $i_4$ is equal to the drain electrode $D_2$ output current of the FET $Q_3$, which is $i_3/2$, and the potential of the node 49 follows the potential of the gate node 50. The drain current from the FET $Q_3$ to the node 51 is half of the current $i_3$ because the FET $Q_2$ is constructed so that both drain currents are always equal to each other when a sufficient source to drain voltage potential is maintained. The current $i_3/2$ applied to the drain electrode $D_2$ of the FET $Q_2$ establishes the current $i_4$ in the drain electrode $D_1$ of the FET $Q_2$ during the interpulse intervals between sampling pulses, which currents must be equal. It is to be noted that the capacitor $C_D$ which is coupled between the gate electrode and the source electrode of the FET $Q_2$ assumes a charge to bias the FET $Q_2$ to pass the current $i_3/2$ while the gate $G_1$ is conducting. If the gate $G_1$ is closed (nonconducting) while the switch $G_2$ is opened (conducting) the voltage $-V$ is applied to the node 50 so that the drain electrode $D_1$ of the FET $Q_3$ remains conducting even though the current increases. Also, the current $i_4$ remains at a value equal to its value just before the sample pulse period. The constant current $i_4$ results from the charge stored on the capacitor $C_D$ maintaining the same gate voltage across the FET $Q_2$ as that prior to the sample pulse period, so that the total current $i_4$ into the drain electrode $D_1$ of the FET $Q_2$ does not change during the sample pulse period. The $-V$ voltage at the drain electrode $D_2$ of the FET $Q_3$ maintains the FET in the balanced split-drain mode during the sample pulse period so that the current applied to the node 51 therefrom is the $i_4$ current plus one-half of the additional signal current. The output current $i_5$, during the sample period, is just the difference between the drain $D_1$ current of the FET $Q_2$ and the drain $D_1$ current of the FET $Q_3$. If the $i_4$ ambient current remains essentially constant and the steady state pulse envelope and other imbalances are cancelled, the output current $i_5$ is then just one-half of the sampling period signal current (heart pressure wave). During the sample pulse period, the current into the drain electrode $D_2$ of the FET $Q_2$ is essentially zero, the drain electrode $D_2$ current from the FET $Q_3$ passing through the gate $G_2$ to the negative supply.

To further explain the operation including the cancellation of ambient photocurrent, when the LED pulse controlled by a timing signal $\phi_4$ is first applied to the pulse generator 16 (FIG. 1), the gate $G_1$ is biased out of condition and the drain current $i_3/2$ to the node 50 from the FET $Q_3$ increases as a result of the LED light pulse sensed by the photodiode 12 (FIG. 1). If the background (ambient) light will remain nearly constant during the brief 31-microsecond pulse ($\phi_4$) that triggers the LED on, the ambient light current will be cancelled since the current $i_4$ remains constant (due to the stored charge on the capacitor $C_D$) and is equal to the ambient light photodetector current $i_3/2$ applied to the node 51 between the LED pulses. The true or total LED current signal which includes the synchronous steady state sample pulse envelope is split into equal parts by the FET $Q_3$, and half is applied to the node 51, the half including the current $i_5$ which is the current in excess of the ambient light current $i_4$. This excess current $i_5$ charges the integrate and hold capacitor $C_c$ through the transmission gate $G_3$ during LED sample pulse periods. Without the synchronous LED light cancellation circuit of the FIGS. 1 and 3, the LED reflected light current would quickly charge and maintain the charge on the capacitor $C_c$ and the voltage at a node 37 (FIG. 1) would be driven to and remain at a high potential close to the $+V$ supply voltage. That high potential condition on the capacitor $C_c$ is precisely what happens a fraction of a second after the finger is placed over the window 22 (FIG. 1) of the sensor and before the synchronous carrier pulse current cancellation control loop 35 including the circuit of FIG. 3 has responded. After the switched capacitor transconductance element 40 of FIG. 3 has had time to respond, the steady state component of the reflected LED light pulse carrier, as well as any residual imbalance from the cancellation circuit of FIG. 2 or unity gain amplifier 43, are cancelled. Thus, the output current $i_5$ consists primarily of just the blood pressure wave photocurrent signal which, after being integrated and passed through the unity gain amplifier 43 represents the envelope of the LED pulse current. Between the LED pulses, the gate $G_7$ responsive to a gating pulse $\overline{\phi}_2$ is open or conductive from the node 25 to the lead 33 so that the parasitic capacitance does not charge during interpulse periods.

It should be noted that this blood pressure wave photocurrent signal, $i_3$ is divided in half by the split drains of the transistor $Q_3$, but is applied directly to the output as $i_5$ without amplification or conversion to a voltage parameter. It should also be noted that sunlight or ambient current in an amount several thousand times greater than the blood pressure wave current can be cancelled (subtracted) by the current $i_4$ at the node 51, leaving a signal current $i_5$ in the range of a few nanoamperes to be integrated across the holding capacitor $C_c$ of a few picofarads, thereby producing a signal in the millivolt range (10 to 50 mV) without amplification. This integrate and hold technique in accordance with the invention, makes possible fast recovery times from the sudden presence and resulting overload of the reflected IR steady state light pulse carrier as the finger is placed over the sensor. This overload is cancelled by the second-order feedback loop 35 (FIG. 1) in times ranging from 1 to 2 seconds rather than 20 to 30 seconds, and eliminates the requirement for digital initialization commands. In another arrangement in accordance with the invention, the switch $G_2$ may be replaced by a suitable storage capacitor to hold the voltage on the node 50 during the $\phi_1$ or the ambient light cancellation period.

Figure 3:
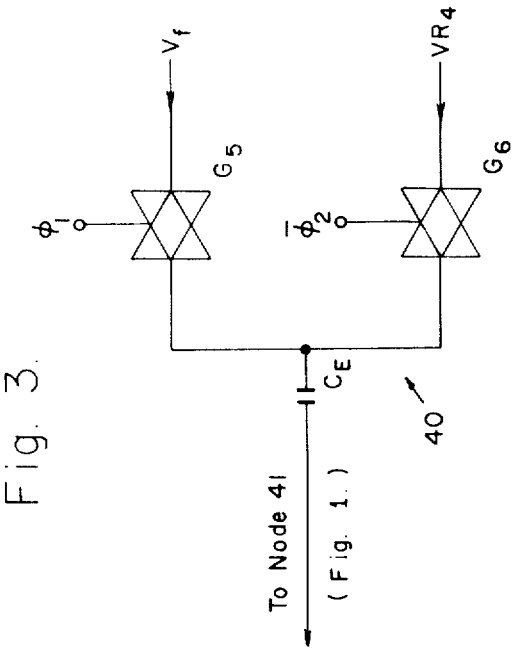
FIG. 3 is a schematic circuit diagram of the switched capacitor transconductance element shown in a perfect second-order feedback loop in the system of FIG. 1 for synchronous steady state pulse carrier light cancellation in accordance with the present invention.

The switched capacitor transconductance element 40 will now be described in relation to the node 41 and the operational amplifier integrator 38 with reference to FIG. 3 as well as to FIG. 1. The object of the transconductance element 40 is to provide cancellation of any pulsed steady state synchronous light components with quick response time (1 to 2 seconds) even though the node 51 (FIG. 2) voltage may be driven to saturation, i.e., into overload. In overload, the element 40 responds with recovery times that are characteristic of the open loop response times ($R_A.C_B$) rather than the closed loop response times ($R_B.C_B$). It should first be noted that one of the reasons for the fast open loop response, and a characteristic of the novel interconnection between the photodetector 12 and the second order synchronous feedback loop including the transconductance element 40, is that a small imbalance between the synchronous current components $i_1$ and $i_2$ will quickly drive the integrating capacitor $C_c$ to produce a high error voltage (nearly equal to the available supply voltage) for restoring the loop to balance.

The synchronous light cancellation loop 39 utilizes the transconductance element 40 comprised of a switched capacitor $C_E$ and two transmission gates $G_5$ and $G_6$. The voltage $VR_4$ is the reference voltage applied to the capacitor $C_E$ during the LED interpulse periods in response to the switching or gating pulses $\overline{\phi}_2$ and the voltage $V_f$ is the error voltage applied to the capacitor $C_E$ during the LED pulse periods in response to the switching or gating pulse $\phi_1$. This switched capacitor transconductance element 40 produces an output current $i_2$ at the node 41 (FIG. 1) proportional to the difference in the reference voltage $VR_4$ and the voltage $V_f$ from the integrating operational amplifier 42. The element 40 provides an equivalent transconductance $g_mE$ of $C_E/T$, where Y is the switching period of the clock signal $\phi_4$, which is 13.67 milliseconds in this exemplary embodiment.

The feedback loop in accordance with the invention is a second-order loop because it has two poles with the first pole being established by $$\left(\frac{1}{g_mE}\right)(C_c)\left(\frac{R_A}{R_B}\right).$$

The second pole is equal to $R_A C_B$ at the operational amplifier integrator 38. The feedback loop is a perfect second order loop because the integrating operational amplifier 42 holds the error voltage at node 25 near $VR_4$ and the error voltage out of the unity gain amplifier 43 need not be increased to correct for an increase in steady state loop stress such as a change in steady state value of the pulse carrier amplitude or an imbalance of the correction provided by the ambient light cancellation circuit 32. The operational amplifier integrator 38 is similar to a conventional type except a phase lead is provided by the stabilization resistor $R_B$.

The ratio $$\frac{R_B}{R_A}$$

determines the high frequency attenuation feedback factor or the amplitude of the cancelling current $i_2$. It is to be noted that the differentiation time constant $R_B C_B$ of the feedback loop allows the high frequency components of the heart blood pressure envelope to be formed on the node 25 as the output signal and that the loop acts to remove the low frequency components of the pressure envelope with the high pass time constant $Y_H = R_B C_B$. It is to be understood that this differentiation in the closed loop forward transfer function is a result of a low frequency integrating operation including $C_B$, $R_A$ and integrating operational amplifier 42 in the feedback or return path 39 of the perfect second-order control loop.

Just prior to the beginning of an LED pulse, nearly all of the current $i_3$ passing to the ambient light cancellation circuit 32 (FIG. 2) is photocurrent resulting from ambient light plus a current $i_6$ which is small bias current (a quiescent current from FET $Q_3$) flowing through the resistor $R_2$ (FIG. 1). At this time, the current $i_4$ is just equal to the input current $i_3/2$ in the "storage current mirror" 48 (FIG. 2). The resulting current difference $i_5$ is nearly zero until light pulses are reflected by a finger being positioned over the sensor 22 (FIG. 1).

A fraction of a second after a finger is placed over the sensor, i.e., over the LED and photodetector, the LED carrier cancellation current $i_2$ is still at its equilibrium value, but the voltage at node 37 (FIG. 1) is quickly driven to a high saturation value by the small error current $i_5$, which is just half of the photocurrent $i_1$ provided by the reflected LED light pulse carrier. As the holding capacitor $C_c$ is driven into saturation within a fraction of a second, nearly half of the total power supply voltage is applied at the output of the unity gain isolation amplifier 43 across the input resistor $R_A$ of the operational amplifier 42. Current resulting from this high fraction of supply voltage applied across the resistor $R_A$ flows through and charges the integrating capacitor $C_B$ in the feedback circuit of the operational amplifier 42. At some point in time, the charge across the capacitor $C_B$ reaches a value such that the output voltage $V_f$ from the amplifier 42 is just sufficient to produce a current $i_2$ at the output of the transconductance element 40 equal to the reflected synchronous steady state LED light component of the current $i_1$. At this point in time, the voltage at the node 37 (FIG. 1) i.e., across the holding capacitor $C_c$, starts to fall rapidly and the loop closes to reach equilibrium with a closed loop time constant determined largely by $R_B \cdot C_B$. This closed loop time constant is much shorter than the open loop time constant $R_A \cdot C_B$ since $R_A$ is usually approximately five to ten times $R_B$ for proper stabilization of the perfect second-order control loop.

Another function of the synchronous light cancellation loop 39 is to correct for any imbalance in the ambient light cancellation circuit 32 which, if not corrected, will produce a small residual component in the output current $i_5$ passed to the integrate and hold section which is just the difference between the current $i_4$ and the exact current $i_3/2$ required for balance. Any such residual component will result in the holding capacitor $C_c$ charging, and the resulting error voltage will charge the integrating capacitor $C_B$ until any errors are perfectly cancelled out by a change in the current $i_2$. An important advantage of this second-order loop arrangement is that cancellation of $i_5$ imbalance current (and steady state pulse current) is achieved with negligible change in the DC differential input error voltage of the amplifier 42, and therefore the DC quiescent voltage at the output of the signal conditioning circuit 24 delivered to the amplifier and bandpass filter 26 (FIG. 1) is quite independent of large changes in ambient light conditions and held closely in value to the reference voltage $VR_4$.

It is to be noted that in the illustrated arrangement in accordance with the invention, the photodetector is a photodiode rather than a phototransistor, because a phototransistor produces high current gain which is a significant factor in slowing the response time of the detector to individual light pulses. The 5 to 6 microsecond response time of the photodiode configuration is significantly less than the 10 to 20 microsecond response time of a phototransistor, particularly if a phototransistor is used in a 32 kHz clock system with a 15 μsec half clock sampling period. Moreover, the longer response time of the phototransistor configuration would bring the primary gain parameter $h_{fe}$, which varies significantly from one phototransistor to another, into strong interaction with system performance, and would adversely affect manufacturing yields because the phototransistor configuration detector response time is directly dependent on $h_{fe}$. Because the arrangement described with reference to FIGS. 1 and 3 uses a switched capacitor transconductance element and yields a high signal-to-noise ratio for blood pressure wave signal voltages without any amplification before the cancellation of background or carrier signals, no transistor $h_{fe}$ gains are required. The fast response of the circuit to individual light pulses may be made even faster than the indicated 5 to 6 microsecond response by minor modifications to the geometry of the input FET $Q_3$ of the asynchronous ambient light cancellation circuit 32 (FIG. 2).

Figure 4:
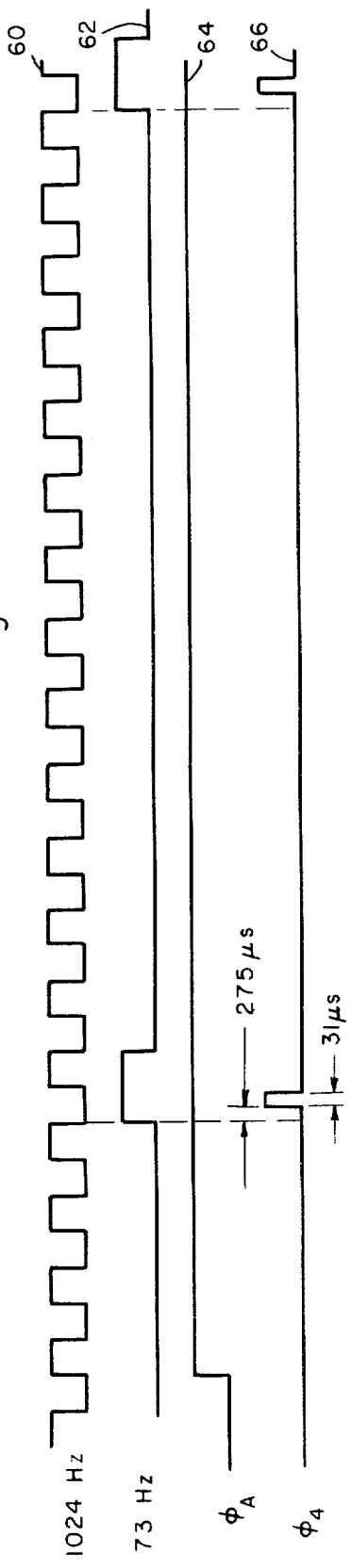
FIG. 4 is a basic logic timing diagram for the system of FIG. 1.

Referring now to the system timing diagram of FIG. 4, the clock pulse generated for the digital watch at nearly 32 kHz (actually 31,744 Hz) is first divided down to 1024 Hz, as shown by a waveform 60, and then further divided down by 14 to produce a low frequency clock at 73 Hz as shown by a waveform 62 for operation of the system in FIG. 1 as a heart pulse rate monitor. This lower rate controls the integrate and hold cycle, but only while the control signal $\phi_A$ of a waveform 64 is turned on by the operator when ready to measure heart pulse rate. The next and every 14th trailing edge (1 to 0 transition) of the 1024 Hz clock of the waveform 60 initiates a 275 μs delay. The LED is then turned on for 31 μs as shown by a waveform 66. The sequence of turning on the LED at this lower rate of 73 Hz continues until the operator has read the heart pulse rate and turns the control signal $\phi_4$ off.

Figure 5:
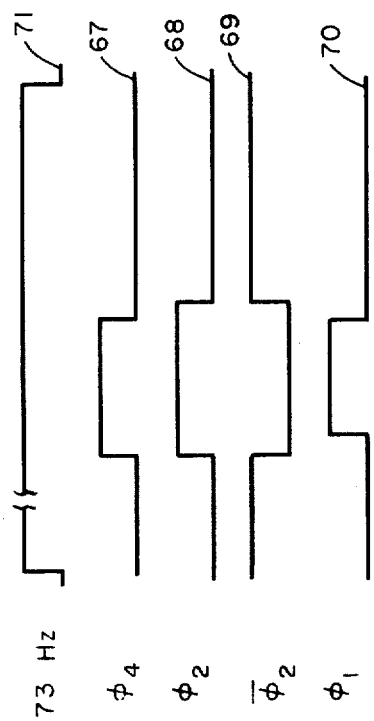
FIG. 5 is a specific logic timing diagram for the circuits of FIGS. 2 and 3.

Referring now also to FIG. 5, each time a $\phi_4$ pulse of a waveform 67 is generated, a $\phi_2$ pulse of a waveform 68 is generated. After a delay of about 0.1 μs, a $\phi_1$ pulse of a waveform 70 is generated, the $\phi_1$ pulse being terminated at the end of the $\phi_4$ pulse. The $\phi_2$ pulse, and its compliment $\overline{\phi_2}$ of the waveform 69 terminates after the $\phi_4$ pulse terminates to complete a pulse wave current sampling cycle. This arrangement of turning on the LED for 31 μsec at a 73 Hz rate (i.e., about every 13.7 milliseconds as shown by a 73 Hz pulse of a waveform 71) conserves power, and allows ample time between LED pulses for the background noise signal to be measured and stored in the capacitor $C_D$ (FIG. 2). Referring now also to FIG. 2, when the pulse $\overline{\phi_2}$ is low (false), the gate $G_1$ stops conducting. Both of the gates $G_1$ and $G_2$ are then open (not conducting for about 0.1 μs). Then the $\phi_1$ pulse of the waveform 70 turns on the gate $G_2$ for control of the voltage at node 50 which would otherwise float, and also controls sampling and integrating of the reflected LED light pulse signal through the gate $G_3$ (FIG. 1). It is to be noted that the gate $G_7$ is controlled by the pulse $\overline{\phi_2}$ of the waveform 69, so that the unity gain amplifier 43 will be disconnected prior to the sampling period $\phi_1$. The 0.1 μs delay in generating the $\phi_1$ pulse allows ample time for the gate $G_1$ to disconnect before shorting the node 50 to the voltage $-V$ through the gate $G_2$, and the 0.1 μs delay in terminating the $\overline{\phi_2}$ pulse after terminating the $\phi_1$ pulse, allows time for the shorting gate $G_2$ to disconnect before again starting to store a charge in the capacitor $C_D$ proportional to the ambient light after the LED pulse terminates.

The feedback loop of section 24 functions as a bandpass filter with a high pass time constant $Y_H$ and a low pass time constant $Y_L$ where:

$$T_L = \frac{1}{g_m} \left( \frac{R_A}{R_B} \right) C_c$$

$$Y_H = R_B C_B$$

The system upper corner frequency $1/(2\pi Y_L)$ is well below any beat frequencies of sampling frequency harmonics and 120 Hz ambient light frequencies.

Referring now to FIG. 6 as well as to FIGS. 1 and 2, the system operation will be further explained including the operation of the second order control loop of the element 24. A waveform 73 shows the photodiode current $i_1$ and the ambient light current which is many times greater in amplitude than the current pulses. It is to be noted that the pulses of FIG. 6 which in the illustrated system are 13.67 milliseconds apart are shown with fewer pulses than actually occur during the illustrated time, for purposes of clarity of illustration. Prior to a time F, the photocurrent $i_1$ of the waveform 73 from the photodiode 12 consists of the ambient light level current plus a small amount of pulsed current from direct coupling between the IR LED 10 and the photodetector 12. The sensor can be constructed so that this current is quite small and in any case cancelled by the balancing current $i_2$ of a waveform 74 provided by the switched capacitor transconductance element 40. Thus, prior to the time F, the current $i_2$ of the waveform 74 removes the small steady state pulse carrier component and the ambient light component is removed by cancellation in the block 48 of FIG. 2. The resulting current $i_5$ of a waveform 75 has an average value of zero prior to time F. It is to be noted that the current $i_5$ pulses are one-half of the current pulse amplitude of $i_1$ in the absence of pulse cancellation. The output of the signal conditioning block 24 is provided by the unity gain amplifier 43 connected to integrate and hold capacitor $C_c$ which neither charges or discharges a significant amount at this time. The output of the amplifier 43 on the lead 25 therefore prior to time F is maintained as a steady state value around $VR_4$ with a small amount of flicker noise present as shown by a waveform 77.

At the time F, a finger is placed over the sensor 22 and within a small fraction of a second, the reflected IR pulse carrier has reached its full steady state value shown by the waveform 73 at a time G. The carrier cancellation current $i_2$ has not changed appreciably at the time G from its steady state value in this time interval from the time F as can be seen by the waveform 74. Consequently, at the time G, nearly the full amplitude carrier current (divided in two by the input split-drain device) is applied as the current $i_5$ to charge the integrate and hold capacitor $C_c$.

Because the capacitor $C_c$ need be only a few (2-4) picofarads and also because there are a few (3-4) picocoulombs in each carrier pulse, the integrate and hold capacitor $C_c$ output can be driven near the positive supply voltage $+V$ limit by just a few (2-3) carrier pulses and the output at node 25 of the unity gain amplifier 43 following the capacitor $C_c$ is also driven near the positive supply voltage limit at the same time. Because the interval between pulses is only 13.7 ms, the output can be driven into saturation within a small fraction of a second as shown by the waveform 77. Also, because the reference voltage $VR_4$ is midway between the supply voltages ($+V$ and $-V$), the output positive swing of the waveform 77 is nearly half the supply voltage and this voltage swing is applied across the resistor $R_A$ of FIG. 1 to discharge the integrating capacitor $C_B$ at a high rate as shown in a waveform 78 by the rapid negative slewing at the output ($V_f$) of the integrating amplifier 42.

As the integrating amplifier 42 slews toward the negative supply, the switched capacitor transconductance element pulsed output current (or charge) of the waveform 74 increases in direct proportion to the difference $VR_4 - V_f$. At a time H, the pulsed output charge of the waveform 74 is just equal to the IR input carrier steady state value as shown by a level 79 of the waveform 73 representing the steady state level of the pulses. The $i_5$ pulsed charging current of the waveform 75 which is the difference between $i_1$ with ambient light removed and $i_2$, therefore reaches a zero value at time H and starts to swing negative. At this time, the capacitor $C_c$ begins to discharge away from the positive supply $+V$ and the unity gain amplifier 43 comes out of saturation as seen by waveform 77. Thus, when the current $i_3$ is intense because of an uncancelled steady state pulse carrier, the voltage increases rapidly at node 25, the voltage $V_f$ falls rapidly and the $i_2$ current increases until the integrating capacitor $C_c$ charging current $i_5$ swings negative at the time H in the waveform 75, resulting in a rapid drop in the output of the unity gain amplifier 43.

The rapid drop in the output voltage of the unity gain amplifier 43 terminates the negative slew of integrating amplifier 42 as shown by the waveform 78. It is to be noted that the compensation resistor $R_B$ introduces phase lead and allows the output of the waveform 78 to assume a positive slope in advance of the time that the voltage drive across $R_A$ of the amplifier 42 has reached $VR_4$ near the time J as can be seen at the waveform 77. Therefore, the output voltage $V_f$ of the amplifier 42 is near a final or stabilized value at time J as shown by the waveform 78.

Although the front end circuitry is settled out by the time J, some additional time is required for the following amplifiers and bandpass filter (26) to settle or stabilize. This requirement of the bandpass filter is on the order of an additional 1-2 seconds so that the entire system is ready to detect the arrival of a systolic pressure wave at a time K.

Figure 7:
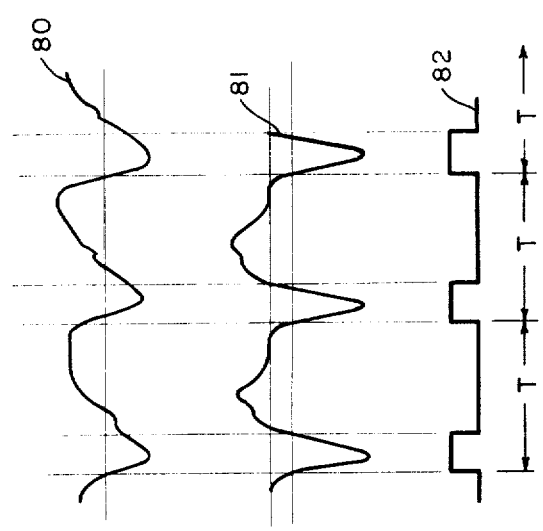
FIG. 7 is a schematic diagram of voltage as a function of time illustrating a typical systolic blood pressure waveform developed by the signal conditioning circuit (Block 24) and the amplifier and bandpass filter (Block 26) of FIG. 1; and the pulse train that is derived from the threshold discriminator (28) of FIG. 1.

A typical blood pressure waveform voltage of the waveform 77 after the time K as monitored by this integrate and hold technique at the rate of 73 Hz is shown in FIG. 7 by a waveform 80. Note that because the arrival of the pressure wave results in dilation of the capillaries and an increase in light absorption, the pressure rise (systolic) period is represented by a negative going voltage and is short compared to the pressure drop (diastolic) period. The signal conditioning section 24 performs both a short time constant (50 ms) integration and 480 ms differentiation on the true pressure waveform, but the time interval from one peak to the next remains exactly the same as for the true pressure waveform. The pulse of a waveform 81 is provided by the amplifier and bandpass filter 26. Measuring the period T from one cycle to the next by detecting the peaks and timing the period between each peak of the waveform 81 thus yields a correct measurement of heart pulse rate, particularly if a running average (i.e., an average period over the last N cycles) is used to determine pulse rate as a reciprocal of the average period. Peak detection is best accomplished by the threshold discriminator 28 (FIG. 1) which converts the pressure wave voltage of the waveform 81, which is the pressure wave of the waveform 80 after amplification and bandpass filtering, to produce a pulse train of a waveform 82.

Period timing is then done by the digital watch timing and pulse rate computation section 18. The timing is done from leading edge to leading edge of each pulse in the pulse train. Pulse rate computation is simply the inverse of the average period measured, i.e., the result of the simple equation $R = 1/T$. The rate thus computed is displayed and updated every 4 systolic intervals, for example, in such a manner as to allow each rate displayed to be clearly read before an update. If the pulse rate being monitored is steady, the average of N periods where N is typically 4, will yield an accurate and steady pulse rate reading. In practice, the operator may leave the system turned on until the rate displayed is steady, which should normally be within 10 seconds, or less.

Figure 9:
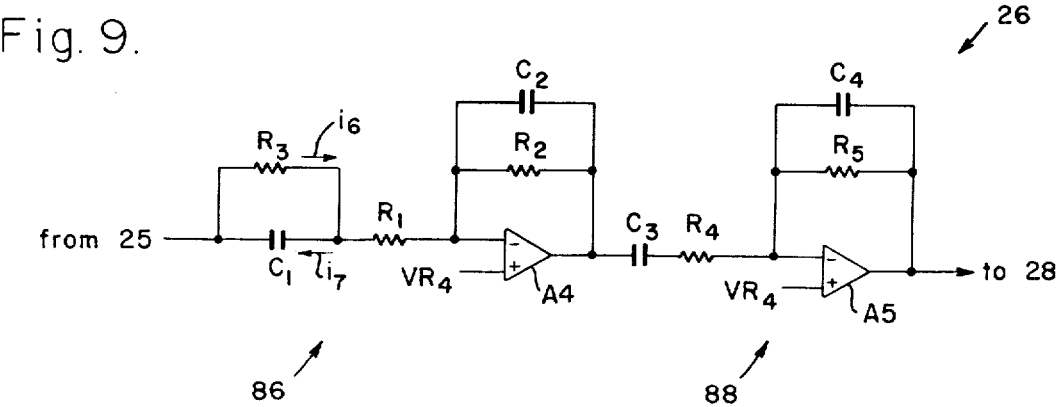
FIG. 9 is a schematic circuit and block diagram of an amplifier and bandpass filter that may be utilized in the system of FIG. 1.

In a preferred embodiment of the illustrated plethysmograph system, the amplifier and bandpass filter 26 of FIG. 1 may be the circuit shown in FIG. 9 in order to compensate the filtering in block 24 so that the uncertainty in detecting the pulse rate at the discriminator 28 is decreased. The combination of the watch circuit and the illustrated amplifier and bandpass filter or the compensation arrangement itself are not believed to be the same invention as claimed herein but they are not dedicated to the public. The amplifier and filter 26 includes stages 86 and 88 each providing differentiation and integration to respectively control the high pass ($f_H'$) and low pass ($f_L'$) corner frequencies of the passband.

The signal from the block 24 at the node 25 is applied through a differentiating capacitor $C_1$ and a resistor $R_1$ to the negative input terminal of an operational amplifier $A_4$ having its positive input terminal coupled to the reference voltage $VR_4$. The signal at the output of the amplifier $A_4$ is fed back through a resistor $R_2$ and parallel coupled capacitor $C_2$ to the negative input terminal thereof. A compensating resistor $R_3$ is coupled in parallel with the capacitor $C_1$ for providing a zero at $f_2$ to cancel the pole at $f_H$ resulting from the differentiation with time constant $Y_H = R_B \cdot C_B$ in the block 24.

The stage 88 includes a capacitor $C_3$ and a resistor $R_4$ serially coupled from the output terminal of the amplifier $A_4$ to a negative input terminal of an operational amplifier $A_5$, the latter amplifier having a positive input terminal coupled to the reference voltage $VR_4$. The signal at the output terminal of the operational amplifier $A_5$ is fed back to the negative input terminal through a parallel coupled resistor $R_5$ and a capacitor $C_4$. The amplified and filtered signal is applied from the output terminal of the amplifier $A_5$ to the discriminator 28.

Referring now also to FIG. 10, an asymptotic passband diagram 89 has a high pass corner frequency $f_H$ and a low pass corner frequency $f_L$ forming the passband at the output of the block 24. The high pass and low pass frequencies are:

$$f_H = \frac{1}{2\pi T_H}$$

where $Y_H = R_B C_B$ and $$f_L = \frac{1}{2\pi T_L}$$

where $$T_L = \left(\frac{1}{g_m E}\right) \frac{R_A}{R_B} C_c.$$

The characteristic output of the amplifier stage $A_4$ without the effect of the block 24 is shown by an asymptotic passband diagram 90 with a high pass corner frequency of $$f_H' = \frac{1}{2\pi T_d}$$

where $Y_d' = (R_1 \| R_3)C_1$. It is to be noted that the symbol $\|$ means that $R_1$ and $R_3$ are in parallel. The diagram 90 has a low pass frequency $$f_L' = \frac{1}{2\pi T_i}$$

where $Y_i = R_2 C_2$. Thus the $C_1$, $R_1$, $R_3$ network determines the high pass frequency and the $R_2 C_3$ network determines the low pass frequency. At a frequency $$f_2 = \frac{1}{2\pi T_3}$$

where $Y_3 = R_3 C_1$, the low frequency asymptote of the passband diagram 90 becomes flat to DC as shown by the solid line. The compensating resistor $R_3$ has the effect of adding a transmission zero which cancels the pole provided by the differentiation time constant $Y_H$ of $R_BC_B$ in block 24. A dotted line 91 shows the low frequency asymptote if the compensating resistor $R_3$ were not included in the circuit. A passband diagram 92 at the output of the amplifier $A_4$ has a high pass asymptote that continues at a constant +1 slope as a result of the combination of the passband of the diagrams 89 and 90. A dotted line 93 shows a +3 slope of the low frequency asymptote which would occur if the compensating resistor $R_3$ were not utilized.

The $A_5$ individual stage characteristic is shown by a passband asymptotic diagram 94 and the $A_5$ composite output characteristic is shown by a passband diagram 96. The high pass and low pass frequencies of the diagrams 94 and 96 are respectively $f_H''$ and $f_L''$ where $$f_H'' = \frac{1}{2\pi T_d''} \text{ and } f_p'' = \frac{1}{2\pi T_i''}.$$

The time constant $Y_d'' = R_4C_3$ and the time constant $Y_i'' = R_2C_2$. It is to be noted that the high pass and the low pass frequencies of the diagram 96 may be represented by two zeroes and five poles. A dotted line 97 having a +3 slope shows the attentuation that would be present in the absence of the compensating resistor $R_3$.

The following are illustrative values of the time constants that may be selected:
$Y_H = 0.48$ seconds
$Y_L = 0.05$ seconds
$Y_3 = 0.48$ seconds
$Y_d' = 0.1$ seconds
$Y_i' = 0.05$ seconds
$Y_d'' = 0.1$ seconds
$Y_i'' = 0.05$ seconds The termination of the slope resulting from the differentiation at the stage 86, is a result of pole and zero cancellation. It is well known in the art that equal zero and pole terms in the respective numerator and denominator of a transfer function expression using complex notation will cancel. To further explain the slope termination, the differentiation action of $R_BC_B$ in the block 24 wil provide a decaying positive voltage in the time domain following the systolic pressure wave and having the time constant $Y_H$. During this decay, it is a well known property of an exponential R-C discharge that the slope (time rate of change) of the voltage will be proportional to the difference between the instantaneous value of the voltage and the quiescent or asymptotic value of the voltage. Stated in another way the ratio of the slope of the input voltage to the input voltage remains constant following an input disturbance. Since the current flow in $C_1$ ($i_7$ in FIG. 9) is proportional to the input voltage slope and opposite in direction to the current flow in $R_3$ ($i_6$ in FIG. 9) which is proportional to the input voltage, it is possible to select the value of $R_3$ such that $i_6$ is equal to and just cancels $i_7$ during the R-C decay. Thus, the zero cancellation of the block 24 pole $R_B.C_B$ is performed by the action of the compensating resistor $R_3$ and the capacitor $C_1$.

The system transfer function provides a sharp cut-off of high frequency noise by the three poles at $f_L$, $f_L'$ and $f_L''$. Also the system transfer function has a fairly sharp low frequency cut off resulting from the two transmission zeros which remove low frequency noise and serve an even more important function which is to reject finger motion artifact. It is to be noted that succeptibility to finger motion is a primary limitation to the illustrated type of plethysmograph system. The pole-zero compensation although decreasing the sharpness of the low frequency cut off, provides the equivalent of a two section low frequency filter which increases system signal to noise ratio beyond that obtainable with a three section filter and improves the overall system response to the heart blood presure wave by eliminating certain overshoot components of the response which would be present in a system with three differentiators.

Figure 11:
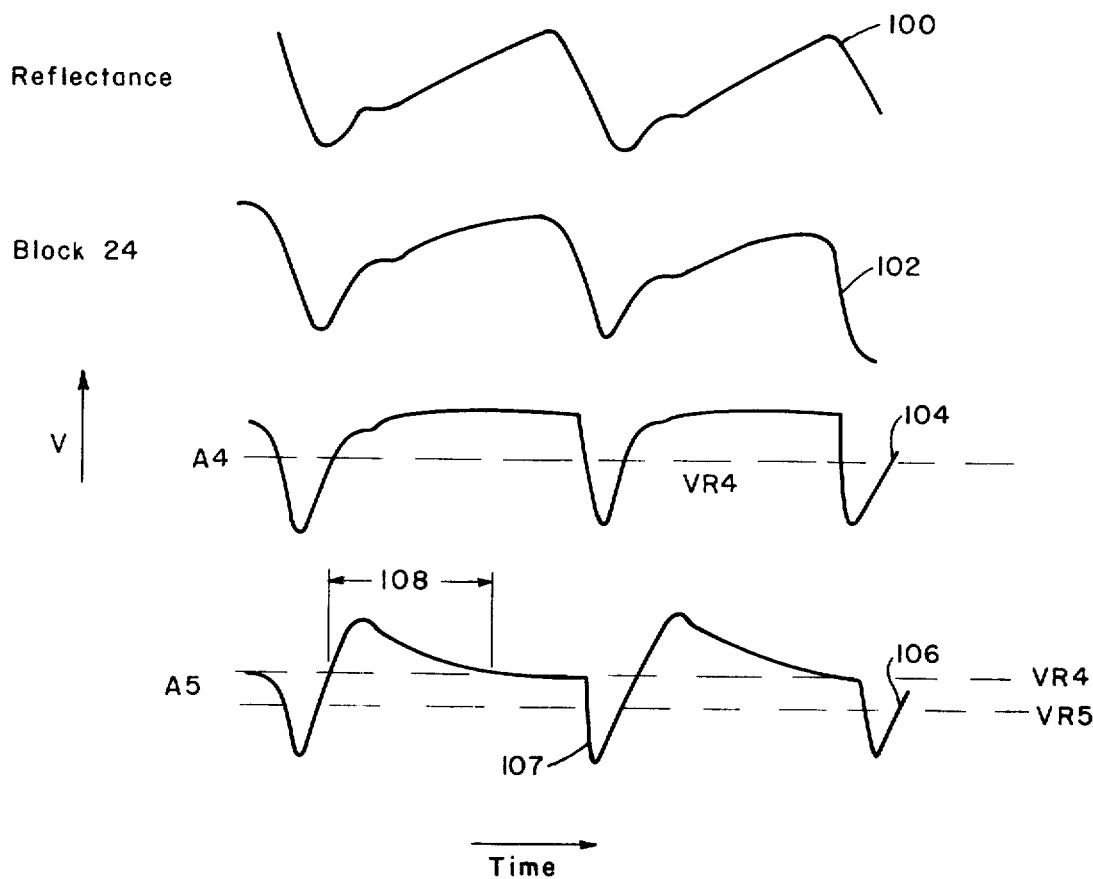
FIG. 11 is a schematic diagram of waveforms of voltage as a function of time for further explaining the operation of the amplifier and bandpass filter of FIG. 9.

The improvement in system response can best be understood by referring also to the waveforms of FIG. 11 which shows an amplified and filtered heart pressure wave that reliably triggers the discriminator. A waveform 100 shows the reflectance signal resulting from the heart blood pressure modulation and a waveform 102 shows the heart blood pressure signal at the output of the block 24. The signal at the output of the amplifier $A_4$ with the pole zero cancellation of the resistor $R_3$ is shown by a waveform 104. The signal at the output of the amplifier $A_5$ is shown by a waveform 106 with the reference voltage level $VR_4$ and the trigger voltage level $VR_5$ at the discriminator 28. The pole zero cancellation deletes the effect of differentiation in the block 24 so that a heart blood pressure wave of the waveform 104 appears to be the result of a single differentiation of the photocurrent into the block 24 which was the original heart blood pressure amplitude modulation. A long time constant differentiation ($R_BC_B$) in the block 24 is now replaced by a short time constant differentiation ($R_1 \parallel R_3.C_1$) at the stage 86. After the second differentiation at the input of amplifier $A_5$, the $A_5$ output is shown by the waveform 106, this second short time constant differentiation returns the voltage waveform rapidly to the amplifier $A_5$ quiescent output voltage which is $VR_4$ and therefore upon arrival of the next systolic pressure wave such as 107, the signal crosses the discriminator trip voltage threshold $VR_5$ with a fast or steep slope. The timing sensitivity to motion artifact is reduced by the steep slope of the leading edge of the systolic pulse 107 because a gradual slope response provides more sensitivity to motion artifact as the time position of the signal crossing the trigger voltage $VR_5$ is more severely modulated by motion artifact signals. Also, the second differentiation of the waveform 106 provides a highly predictable starting voltage ($VR_4$). It should be noted that at higher rates, the starting points will move closer to the back kick such as at 108 produced by the preceding pulse so that the systolic pulse starting voltage is displaced from the voltage $VR_4$. However, at higher pulse rates, especially those produced by exercise, the heart rhythm generally becomes more uniform so that the displacement of the starting voltage displacement from $VR_4$ has no contribution on a beat to beat basis.

Laboratory investigations based in a four interval pulse average have shown that at 5-10 PPM (Pulse Per Minute) uncertainty can be expected with a single slow integration and differentiation arrangement and a 3-5 PPM uncertainty can be expected with an uncompensated triple differentiation of the illustrated system without the resistor $R_3$. Tests have shown that with the two differentiator pole zero compensation of the preferred embodiment, only a 1-2 PPM uncertainty is to be expected.

In the illustrated system, it is desirable to have $R_BC_B$ very large to decrease, at the amplifier $A_4$, the DC gain in proportion to the AC gain, that is $R_3/R_1$ should be a large ratio to insure wide DC operating margins. The time constants $Y_H$ and $Y_3$ must be equal, that is, $R_BC_B$ must equal $R_3C_1$. In an integrated circuit layout such as in a watch, the size of the capacitor $C_B$ is limited. The value of $R_B$ is limited by the minimum allowable value of the low pass frequency $f_L$, which if too small, will restrict the passage of desired high signal frequency components through the front end (block 24). The size of the resistor $R_3$ is therefore determined by two front end constraints as well as the limited maximum value of the capacitor $C_1$. Thus, the long time constant in the block 24 is required for proper system operation and the pole-zero cancellation provides improved pulse response and signal to noise performance.

The input signal conditioning circuit 24 (FIG. 1) is also useful in other applications where cancellation of ambient light is important. However, for some applications, such as for IR ranging or electronic games, extraction of a small amplitude modulation signal and synchronous light cancellation is not required. In such an application it is only necessary to detect the presence of a high frequency (25 kHz for example) IR carrier, and therefore there is also no requirement for the input signal conditioning circuit to be a part of a second order control loop.

Figure 8:
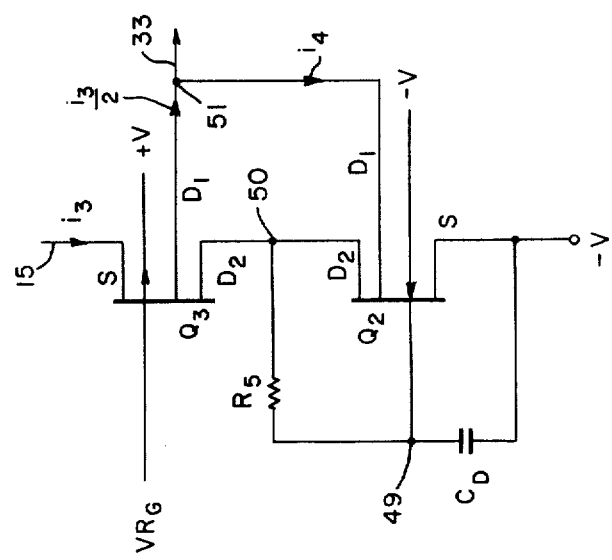
FIG. 8 is a schematic circuit diagram of a simplified embodiment of the ambient light cancellation circuit of FIG. 2 for use in arrangements where only asynchronous ambient light is to be cancelled, and the transmitting device is pulsed at some rate which is high as compared to variations in the ambient light.

A second simplified embodiment shown in FIG. 8, which will now be described, is suitable for such applications where merely the presence of a pulsed IR signal must be detected in the presence of bright ambient light, and where IR source power consumption is not so limited as in a wristwatch. In such an application, the LED may, for example, be driven at a high (25 kHz) rate with a high (50%) duty cycle. For convenience, the same reference numerals as in FIG. 2 are retained in this simplified embodiment for the same components.

This simplified embodiment provides for cancellation of ambient light in a similar manner as the first embodiment of FIG. 2. The primary difference is that the transmission gate $G_1$ has been replaced by a resistor $R_5$. Also, the gate $G_2$ is omitted. The circuit is useful for detection of the pulsed IR photocurrent signal in those applications which do not require synchronous demodulation of the IR signal, and simply require the IR signal to be separated from the ambient light, and where subsequent AC amplification of the detected pulse IR signal may be provided.

Light received by a photodetector such as 10 (FIG. 1) is converted to photocurrent $i_3$, and this photocurrent is split into approximately equal parts by the two drains of the FET (P-channel) $Q_3$. The FET (N-channel) $Q_2$ functions as a low pass filter and current mirror, causing a current to flow in one drain $D_1$, equal to the current in drain $D_2$, which is low in frequency compared to the cutoff of the filter and is not shunted to ground by the filter and therefore is mirrored into drain $D_1$. Therefore, the mirror structure causes only the low frequency components of the current from the transistor $Q_3$ to the node 51 to be cancelled, namely the ambient light, and none of the high frequency components of the pulsed IR. The whole structure from the lead 15 to the lead 33 of FIG. 8 therefore acts like an extremely wide dynamic range high-pass filter.

The most important aspect of ambient light cancellation in this simplified embodiment is sunlight photocurrent cancellation. Sunlight photocurrent from some large area PIN photodiodes can be as high as 1 ma, for example, if the input resistance of a load is in the range of 100 kilo-ohms a supply voltage in excess of 100 V would be required to accommodate the 1 ma photocurrent. With cancellation of this sunlight photocurrent by 95 to 99%, it is possible to operate the same load with less than a 10 volt supply.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A pulse rate measuring system for receiving during sample pulse intervals, a pulsed photocurrent signal including an ambient light photocurrent signal and a pulsed photocurrent carrier signal which is amplitude modulated by a heart blood pressure signal, and for providing said heart blood pressure signal to an output terminal, said rate measuring system comprising a sensor including a pulsed light source and a photodiode having an anode and a cathode with the cathode coupled to a first source of reference potential, the anode providing said pulsed photocurrent signal, ambient light cancellation means directly coupled to the anode of said photodiode for cancelling the ambient light photocurrent signal during pulse intervals, first integrator means coupled to said ambient light cancellation means for receiving at least a portion of the pulsed photocurrent signal from said ambient light cancellation means during sample pulse intervals and for integrating and holding said heart blood pressure signal, and first integrator means providing heart blood pressure and error voltage signals to an output terminal, and feedback means coupled between the output terminal of said first integrator means and the anode of said photodiode and including a second integrator means and a switched transconductance element, said second integrator means including an operational amplifier having an output terminal coupled to said switched transconductance element and having first and second input terminals with said first input terminal coupled to respond to said error voltage signals to control said switched transconductance element to provide a cancelling current during sample pulse intervals, and a second source of reference potential coupled to said second input terminal of said operational amplifier for maintaining the potential substantially constant at said first input terminal of said operational amplifier.

2. The combination of claim 1 in which said ambient light cancellation means includes first and second field-effect transistors having split-drain electrodes and with a source electrode of said first transistor being coupled to the anode of said photodiode, the first drain electrodes of said first and second transistors being coupled together and to said first integrator means and the second drain electrodes of said first and second transistors being coupled together at a node, capacitive means coupled between a source electrode and a gate electrode of said second transistor, and gating means coupled to said node, to a third source of reference potential and to said capacitive means for connecting said capacitive means to said node during periods between said sample pulse intervals and for disconnecting said capacitive means from said node and applying said third reference potential to said node during said sample pulse intervals.

3. The combination of claim 1 in which said switched transconductance element includes switched comparison means for comparing a signal from said second integrator means with a third reference potential and providing cancelling current during said sample pulse intervals.

4. The combination of claim 1 in which said first integrator means includes switching means coupled to said ambient light cancellation means, an integrating capacitor coupled between said switching means and a third source of reference potential and a unity gain operational amplifier having a first input terminal coupled to said integrating capacitor and an output terminal connected to said rate measuring system output terminal.

5. The combination of claim 4 in which said switching means includes a first switch to conduct from said ambient light cancellation means to said integrating capacitor during said sample pulse intervals and a second switch coupled from said ambient light cancellation means to a second input terminal of said unity gain operational amplifier and to said rate measuring system output terminal for conducting between said sample pulse intervals.

6. The combination of claim 1 in which said operational amplifier of said second integrator means further includes a first resistor coupled between the output terminal of said first integrator means and the first input terminal of said operational amplifier, a capacitor and a resistor series coupled between said first input terminal and said output terminal of said operational amplifier and a third source of reference potential coupled to said second input terminal of said operational amplifier.

7. The combination of claim 1 further including discriminator means coupled to said rate measuring system output terminal, rate computation means coupled to said discriminator means and display means coupled to said rate computation means.

8. A system for receiving pulsed photocurrent during sample pulse intervals, said photocurrent including ambient light photocurrent, a steady state pulsed carrier photocurrent and a heart blood pressure modulation photocurrent, and applying a heart blood pressure modulation wave to an output terminal, said system comprising
a photodiode for providing said pulsed photocurrent,
asynchronous cancellation means having an input terminal directly coupled to said photodiode for cancellation of said ambient light photocurrent,
integrate and hold means coupled from said asynchronous cancellation means to said output terminal for providing an error voltage signal proportional to the uncancelled portion of the steady state pulsed carrier photocurrent and for providing a heart pressure modulation wave, and
feedback means coupled between said output terminal and said input terminal of said asynchronous cancellation means, said feedback means including means for integrating and storing said error voltage signal and holding the steady state value of said error voltage on said output terminal independent of subsequent changes of said steady state pulsed carrier photocurrent value.

9. The combination of claim 8 in which said feedback means is a second-order feedback loop.

10. The system as defined in claim 9 in which said second-order feedback loop includes control means for maintaining a feedback voltage at a level $V_f$ proportional to the integral of the difference between said error voltage signal out of said integrate and hold means and a reference voltage $VR_4$, and means for producing a feedback current to the direct coupled input terminal of said asynchronous cancellation means that is proportional to the difference $VR_4 - V_f$.

11. The system as defined in claim 10 wherein said means for producing a feedback current is a switched capacitor transconductance means comprised of a capacitor, a first transmission gate connecting a source of said feedback voltage $V_f$ to said capacitor, a second transmission gate connecting a source of said reference voltage $VR_4$ to said capacitor, means for turning on said second transmission gate while said first transmission gate is turned off between said pulse intervals, and means for turning on said first transmission gate while said second transmission gate is turned off during said pulse intervals.

12. The system as defined in claim 11 further including detecting means coupled to said system output terminal for detecting peaks of voltage in said heart pressure modulation wave developed by said integrate and hold means, second means couled to said first means for computing the rate of said peaks, and third means coupled to said second means for displaying said rate.

13. The system as defined in claim 12 wherein said system is a reflectance plethysmograph having a light emitting diode mounted at a selected distance from said photodiode, and means for periodically triggering said light emitting diode to provide light pulses, wherein said photodiode is mounted to receive at least a portion of the energy of said light pulses emitted from said light emitting diode.

14. A system comprising a photodiode to detect pulsed light during light pulse periods in the presence of asynchronous ambient light, said photodiode responding to said pulsed light to provide an amplitude modulated pulsed carrier photocurrent, signal conditioning means for cancellation of asynchronous ambient light photocurrent for the photocurrent produced by said photodiode, said signal conditioning means connected directly to said photodiode to receive photocurrent, integrate and hold means coupled to said signal conditioning means for integrating and holding a voltage proportional to said pulsed carrier photocurrent over a succession of light pulse periods, a second-order feedback loop coupled from an output terminal of said integrate and hold means to an input terminal of said signal conditioning means, said feedback loop including switched transconductance means for switching a charge of current proportional to a difference voltage between a reference voltage and an output voltage of said integrate and hold means and providing a feedback signal to the input terminals of said signal conditioning means during light pulse periods.

15. The improvement of claim 14 wherein said switched transconductance means is comprised of a series connected capacitor and two gates that are alternately switched into conduction, one gate being switched into conduction for connecting said capacitor to said reference voltage, and one gate being switched into conduction for connecting said capacitor to said output voltage of said integrate and hold means.

16. A system including a photodiode for detecting pulsed light during light pulse periods and for detecting the presence of asynchronous ambient light between said pulse periods and signal conditioning means coupled to said photodiode for cancellation of said asynchronous ambient light photocurrent from photocurrent produced by said photodiode during said pulse periods, said signal conditioning means being comprised of a split-drain field-effect transistor having a source element coupled to said photodiode and storage current mirror means coupled between the split-drain elements of said field-effect transistor, a first one of said split-drain elements serving to provide to said current mirror means between said pulse periods, an output signal proportional to asynchronous ambient light photocurrent received at said source element of said transistor, and a second one of said split-drain elements providing to said current mirror means during said pulse periods, a photocurrent proportional to said asynchronous ambient light photocurrent sampled between pulse periods and providing to an output terminal of said signal conditioning means, a photocurrent signal with the asynchronous ambient light photocurrent cancelled.

17. A pulsed plethysmograph instrument for heart pule rate measurement and display comprising
   a light emitting diode;
   means for periodically pulsing said light emitting diode to emit pulse of IR radiation during sample pulse intervals;
   a photodiode for detecting at least a portion of said radiation and producing a photodiode current proportional to the radiation received, said photodiode current including an asynchronous ambient light current and a pulsed carrier current including a steady state pulsed carrier component and an amplitude modulated heart blood pressure component,
   signal conditioning means having an input terminal connected to receive said current produced by said photodiode without amplification for producing at an output terminal a voltage signal proportional to said amplitude modulated heart blood pressure component, said signal conditioning means including,
   means for cancellation of current due to asynchronous ambient light detected by said photodiode, and
   means for cancellation of the steady state pulsed carrier component of the current produced by said photodiode during said sample pulse intervals;
   pulse discriminator means for detecting systolic pulses in said voltage signal produced at the output terminal of said signal conditioning means;
   means for computing the pulse rate of the detected systolic pulse; and
   means for displaying the pulse rate.

18. A pulsed plethysmograph as defined in claim 17 wherein said means for cancellation of current due to asynchronous ambient light is comprised of
   a storage capacitor,
   first and second gates,
   means for dividing said current received from said photodiode in two current paths, a first path for producing an output current to the means for cancellation of the steady state pulsed carrier component and a second path for producing a current to said storage capacitor through said first gate to store in said capacitor a voltage proportional to said asynchronous ambient light photocurrent amplitude,
   means for controlling said second gate to conduct said current in said second path between sample pulse intervals,
   means for switching current conduction in said second path through said first gate during said sample pulse intervals, and
   means responsive to the voltage stored in said capacitor for shunting from said output current in said first path a current equal to the current that produced the stored voltage on said capacitor, whereby ambient light present is cancelled from said output current during said sample pulse intervals.

19. A pulsed plethysmograph as defined in claim 18 whereiln said means for cancellation of the steady state pulsed carrier component of the current produced by said photodiode during detection of reflected IR radiation pulses is comprised of
   first integrating means coupled to said means for cancellation of current due to asynchronous ambient light for integrating said output current during said sample pulse intervals and for storing integrated current during periods between integrations to provide a voltage signal at said output terminal of said signal conditioning means, and
   a second-order feedback loop coupled between said output terminal and said input terminal of said signal conditioning means, said loop including second integrating means and switched means for controlling feedback current to be proportional to the difference between a reference voltage and the output voltage of said second integrating means during said sample pulse periods, whereby the pulsed steady state carrier component of the reflected IR radiation is cancelled.

20. In an apparatus having a photodiode for detecting pulsed light energy in the presence of ambient light, signal conditioning means connected to receive at an input terminal a photocurrent from said photodiode without amplification for producing at an output terminal a current signal proportional to said pulsed light energy with cancellation of photocurrent due to said ambient light, said signal conditioning means comprising
   a storage capacitor,
   means for dividing said photocurrent received from said photodiode into two equal current paths, a first path for producing a current to said output terminal, and a second path for producing a voltage on said storage capacitor proportional to the low frequency components of current from said photodiode in said second path, and
   means responsive to said voltage stored on said capacitor for shunting from said output terminal a current equal to said low frequency components of current from said photodiode in said second path due to ambient light.

21. In an apparatus having a photodiode for detecting pulsed light provided by a source of light pulses in the presence of ambient light, signal conditioning means connected to receive at an input terminal a photocurrent from said photodiode for producing at an output terminal a current signal proportional to said pulsed light with cancellation of photocurrent due to said ambient light, comprising
   a storage capacitor,
   a first gate,
   means for equally dividing said photocurrent received from said photodiode into two current paths, a first path for providing a current to said output terminal, and a second path for providing a current to said storage capacitor through said first gate to store on said capacitor a voltage proportional to the current amplitude through said second path, a second gate coupled to said second path, means coupled to said first gate for switching off current conduction in said second path through said first gate for a period substantially equal to the period of said light pulses, each time said source provides a light pulse, means coupled to said second gate for switching on said second gate to conduct said current in said second path for periods while current conduction through said first gate is switched off, and means responsive to the voltage stored on said capacitor for shunting from the current in said first path a current equal to the current that produced the stored voltage on said capacitor, whereby photocurrent due to ambient light is cancelled from said output terminal during the period when said photodiode is receiving said pulsed light while said first gate is not conducting and said second gate is conducting current.

22. A signal cancelling circuit responsive to a pulsed input signal, said input signal including an asynchronous signal and a modulated pulsed carrier signal, said circuit cancelling said asynchronous signal and applying to an output terminal a signal proportional to said modulated pulsed carrier signal, said circuit comprising a storage capacitor, first transistor means responsive to said pulsed input signal for equally dividing said input current into first and second paths, said first path being coupled to said output terminal, a first gate coupling the second path and said storage capacitor, second transistor means having first and second paths respectively coupled to the first and second paths of said first transistor means, the conduction through said second path being controlled during pulses, a source of reference potential, a second gate coupled between said source of reference potential and said second path of said first and second transistor means, and timing means coupled to said first and second gates for biasing said first and second gates respectively conducting and nonconducting between the pulses and respectively nonconducting and conducting during the pulses.

23. The combination of claim 22 in which said first and second transistor means are respective first and second split gate field-effect transistors with the source of said first field-effect transistor being responsive to said pulsed input signal and the first and second paths of said first and second transistor means respectively being first and second drains of said first and said second field-effect transistors.

24. The combination of claim 23 in which said first and second field-effect transistors are of opposite conductivity types.

25. Signal conditioning means responsive to an input current signal including an asynchronous current signal and a pulsed current carrier signal for providing at an output terminal a signal proportional to said pulsed current carrier signal with cancellation of said asynchronous current signal comprising first and second split-drain field-effect transistors each having first and second drain electrodes respectively coupled together and with the second drain electrodes coupled to said output terminal, each transistor having a source electrode and a gate electrode, the source of said first field-effect transistor being responsive to said input current signal, a source of a first reference potential and a source of a second reference potential respectively coupled to the gate electrode of the first field-effect transistor and the source electrode of said second field-effect transistor, a resistor coupled between the second drain electrodes of said transistor and the gate electrode of said second field-effect transistor, and a capacitor coupled between the gate electrode of said second field-effect transistor and said second source of reference potential.

* * * * *